(12) United States Patent
Ashibu

(10) Patent No.: US 12,744,339 B2
(45) Date of Patent: Sep. 22, 2026

(54) CONNECTOR AND CONNECTOR ASSEMBLY

(71) Applicant: Japan Aviation Electronics Industry, Limited, Tokyo (JP)

(72) Inventor: Kenta Ashibu, Tokyo (JP)

(73) Assignee: JAPAN AVIATION ELECTRONICS INDUSTRY, LIMITED, Tokyo (JP)

( * ) Notice: Subject to any disclaimer, the term of this patent is extended or adjusted under 35 U.S.C. 154(b) by 280 days.

(21) Appl. No.: 18/515,956

(22) Filed: Nov. 21, 2023

(65) Prior Publication Data

US 2024/0222890 A1 Jul. 4, 2024

(30) Foreign Application Priority Data

Dec. 28, 2022 (JP) ................................ 2022-211312

(51) Int. Cl.
*H01R 12/59* (2011.01)
*A61B 5/00* (2006.01)
*H01R 4/50* (2006.01)

(52) U.S. Cl.
CPC ......... *H01R 12/592* (2013.01); *A61B 5/6804* (2013.01); *H01R 4/5066* (2013.01)

(58) Field of Classification Search
CPC .... H01R 12/592; H01R 4/5066; A61B 5/6804
USPC ................................................ 439/329, 492
See application file for complete search history.

(56) References Cited

U.S. PATENT DOCUMENTS 3,757,219 A * 9/1973 Aksu .................. G01R 1/07328 324/755.05
4,948,374 A * 8/1990 Carter .................... H01R 12/62 439/329
8,465,328 B2 * 6/2013 Lida ......................... H01R 4/58 439/660
2012/0149246 A1 6/2012 Iida et al.
2015/0024619 A1 * 1/2015 Thies ....................... H01R 4/48 439/329
2016/0141781 A1 * 5/2016 Huang .................. H01R 12/77 439/329

(Continued)

FOREIGN PATENT DOCUMENTS

JP S49111764 U 9/1974
JP H6072190 U 10/1994
JP 2003243071 A 8/2003

(Continued)

*Primary Examiner* — Gary F Paumen
(74) *Attorney, Agent, or Firm* — MUNCY, GEISSLER, OLDS & LOWE, P.C.

(57) ABSTRACT

The connector includes a sheet member having flexibility and insulating property, and including a fitting portion to be fitted to a counter connector and a mounting portion to be mounted on a mounting object, a flexible conductor disposed at least on a top surface of the sheet member, and a contact member and a positioning member disposed in the fitting portion of the sheet member, and the flexible conductor includes a first connection portion disposed in the fitting portion of the sheet member and electrically connected to the contact member, a second connection portion disposed in the mounting portion of the sheet member and to be electrically connected to the wiring portion of the mounting object, and a joint portion joining the first connection portion and the second connection portion to each other.

12 Claims, 10 Drawing Sheets

(56) References Cited

U.S. PATENT DOCUMENTS

| | | | |
|---|---|---|---|
| 2021/0098914 | A1 | 4/2021 | Hashiguchi |
| 2022/0158373 | A1 | 5/2022 | Komoto |

FOREIGN PATENT DOCUMENTS

| | | | |
|---|---|---|---|
| JP | 2021057294 | A | 4/2021 |
| JP | 202280493 | A | 5/2022 |
| WO | WO2011/021937 | A1 | 2/2011 |
| WO | WO2019/155237 | A1 | 8/2019 |

* cited by examiner

FIG. 3
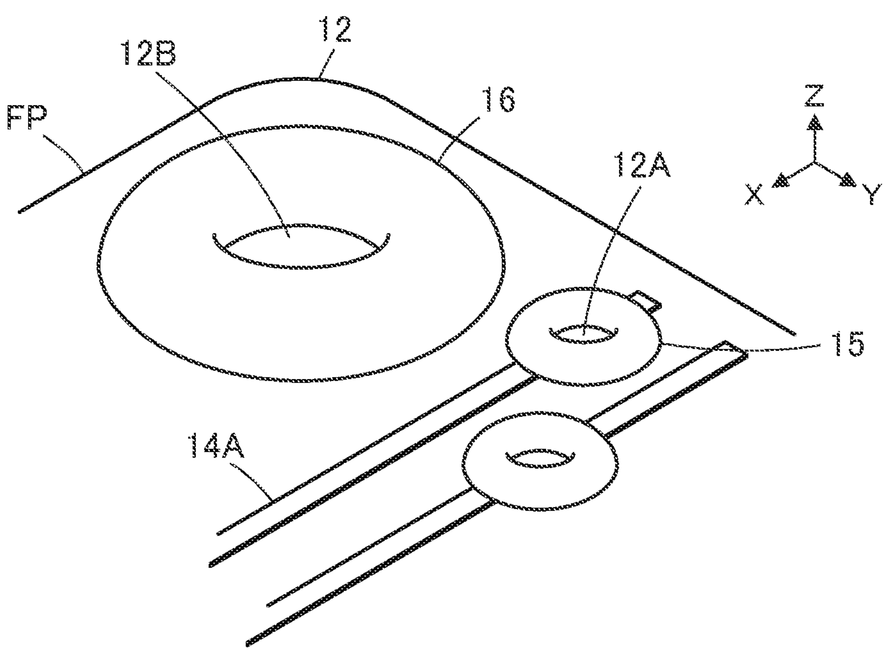
FIG. 4
12A 15 14A 16 12
Z
X
FIG. 5
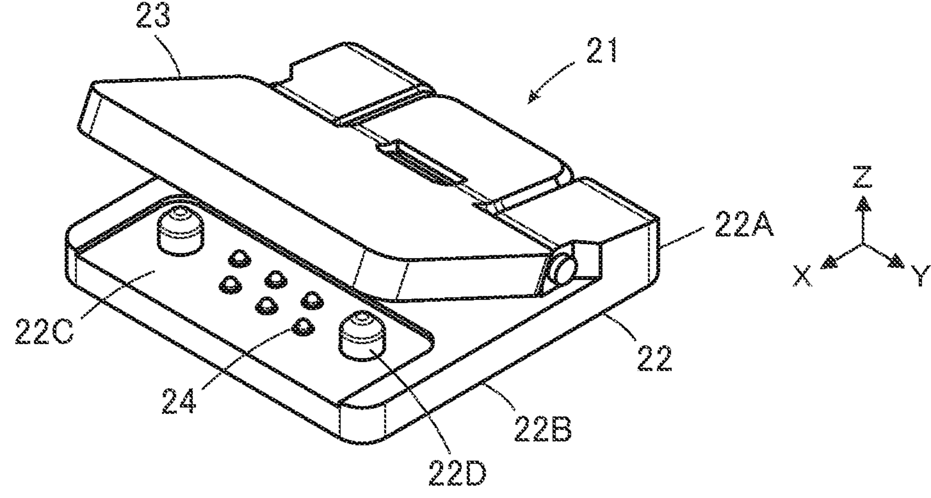

FIG. 9
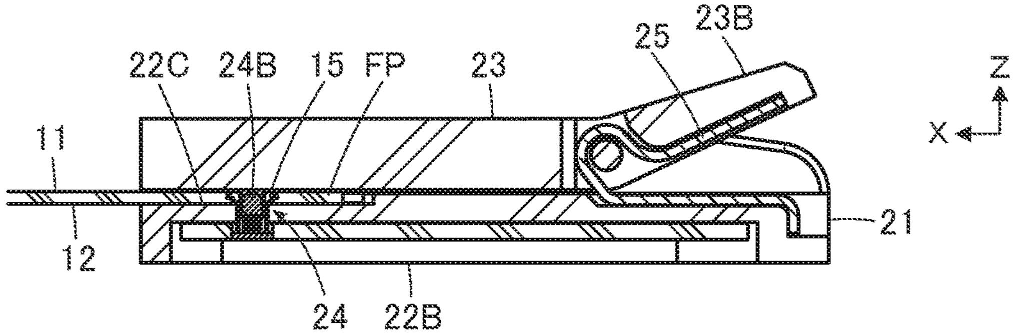
FIG. 10
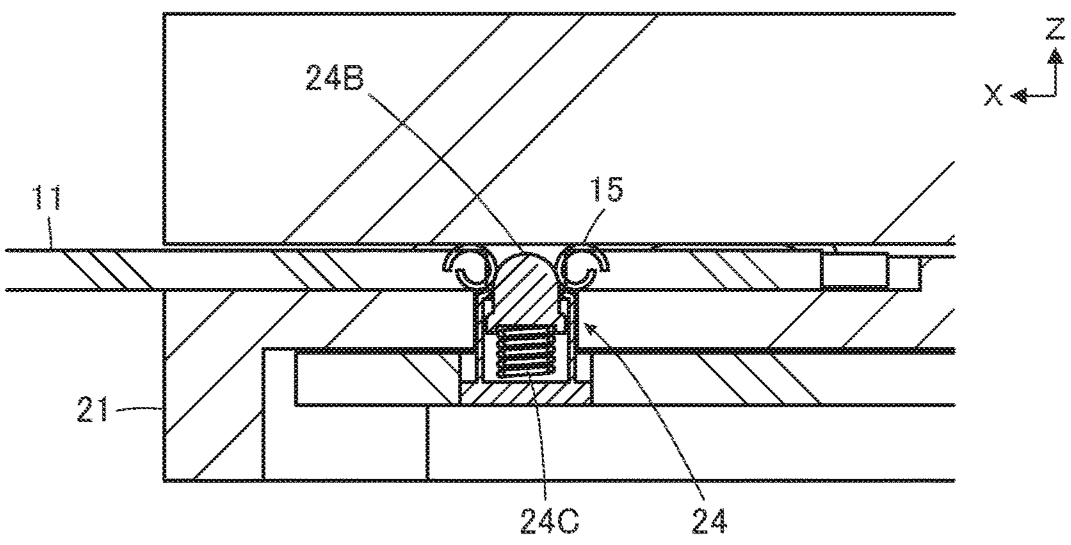
FIG. 11
14
12
31
16
X
Y
C
C
14A
35
MP
FP

CONNECTOR AND CONNECTOR ASSEMBLY

BACKGROUND OF THE INVENTION

The present invention relates to a connector, particularly to a connector that is mounted on a mounting object such as a garment and is fitted to a counter connector.

The present invention also relates to a connector assembly including such a connector and a counter connector.

In recent years, attention has been drawn to so-called smart clothes that can obtain user's biological data such as the heart rate and the body temperature only by being worn by the user. Such smart clothes have an electrode disposed at a measurement site, and when a wearable device serving as a measurement device is electrically connected to the electrode, biological data can be transmitted to the wearable device.

The electrode and the wearable device can be interconnected by, for instance, use of a connector connected to a wiring portion drawn from the electrode.

As a connector of this type, for example, JP 2022-80493 A discloses a connector shown in FIGS. 26 and 27. The connector includes a connector body 1 made of an insulating material. The connector body 1 includes a first insulator 3 disposed on a top surface of a garment 2 and a second insulator 4 disposed on a bottom surface of the garment 2, and is attached to the garment 2 together with a tab sheet 5. The tab sheet 5 is used to reinforce the garment 2. A plurality of contacts 6 are retained by the first insulator 3, and the contacts are connected to a wiring portion 7 disposed on the garment 2.

Using the connector as a garment-side connector, a module-side connector (not shown) is fitted to the garment-side connector, whereby biological data can be transmitted to a measurement module to enable measurements and other actions.

In the meantime, since the first insulator 3 and the second insulator 4 constituting the connector body 1 are made of an insulating material having low flexibility, and since the second insulator 4 is particularly disposed on the bottom surface of the garment 2, a user may feel uncomfortable, degrading comfortableness in wearing the garment 2.

SUMMARY OF THE INVENTION

The present invention has been made in order to solve the conventional problem described above and aims at providing a connector capable of suppressing deterioration in comfortableness in wearing even when the connector is mounted on a garment or another mounting object.

The present invention also aims at providing a connector assembly composed of such a connector and a counter connector.

The connector according to the present invention is a connector configured to be mounted on a mounting object and fitted to a counter connector, the mounting object having a wiring portion disposed thereon, the connector comprising:

- a sheet member having flexibility and insulating property;
- a flexible conductor disposed at least on a top surface of the sheet member;
- a contact member having conductivity that is attached to the sheet member and configured to be electrically connected to a counter contact of the counter connector; and
- a positioning member configured to position the sheet member with respect to the counter connector,
- wherein the sheet member includes a fitting portion to be fitted to the counter connector, and a mounting portion to be mounted on the mounting object,
- the contact member and the positioning member are disposed in the fitting portion of the sheet member, and
- the flexible conductor includes a first connection portion disposed in the fitting portion of the sheet member and electrically connected to the contact member, a second connection portion disposed in the mounting portion of the sheet member and to be electrically connected to the wiring portion of the mounting object, and a joint portion joining the first connection portion and the second connection portion to each other.

The connector assembly according to the present invention is a connector assembly comprising:

- the above-described connector; and
- the counter connector to which the connector is fitted.

BRIEF DESCRIPTION OF THE DRAWINGS

FIG. 3 is a partial perspective view showing the connector used in Embodiment 1.

FIG. 4 is a cross-sectional view taken along line A-A in FIG. 2.

FIG. 5 is a perspective view showing a counter connector used in Embodiment 1.

FIG. 9 is a partial cross-sectional view showing the connector assembly according to Embodiment 1.

FIG. 10 is an enlarged view of a main part of FIG. 9.

FIG. 11 is a plan view showing a connector used in Embodiment 2.

DETAILED DESCRIPTION OF THE INVENTION

Embodiments of the present invention are described below based on the accompanying drawings.

Embodiment 1

Figure 1:
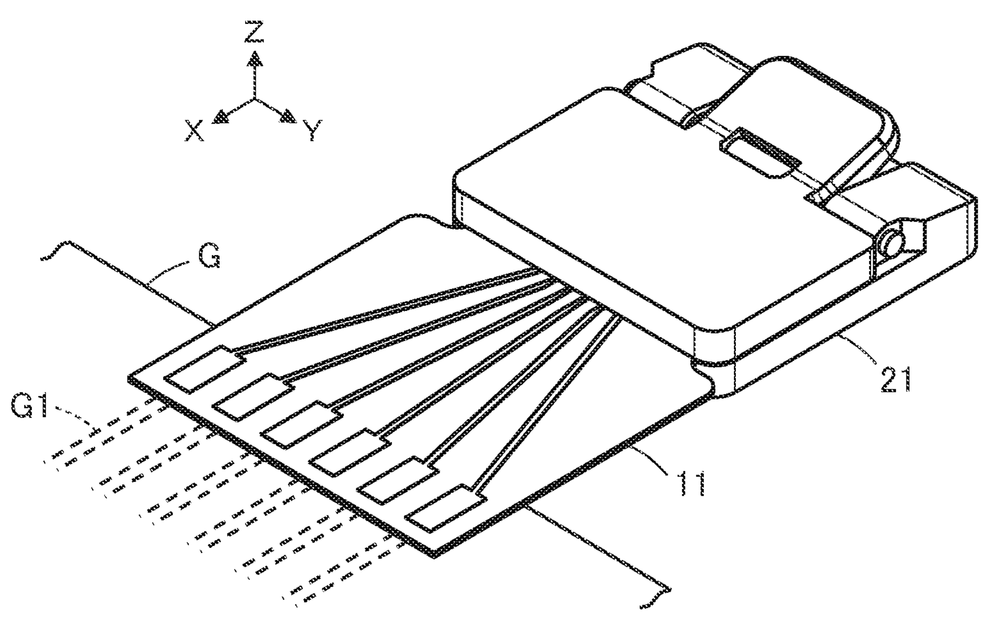
FIG. 1 is a perspective view showing a connector assembly according to Embodiment 1.

FIG. 1 shows a connector assembly according to Embodiment 1. The connector assembly includes a connector 11 and a counter connector 21 to which the connector 11 is fitted.

The connector 11 has a sheet shape and is fitted to the counter connector 21 with part of the connector 11 being inserted inside the counter connector 21.

FIG. 1 shows a state where the connector 11 is mounted on a garment G, i.e., a mounting object to be thus used as a garment-side connector and is fitted to the counter connector 21 that serves as a module-side connector.

For convenience, the connector 11 having a sheet shape is defined as extending along an XY plane, the direction from the connector 11 to the counter connector 21 is referred to as "−X direction," and the direction perpendicular to an XY plane is referred to as "Z direction."

Figure 2:
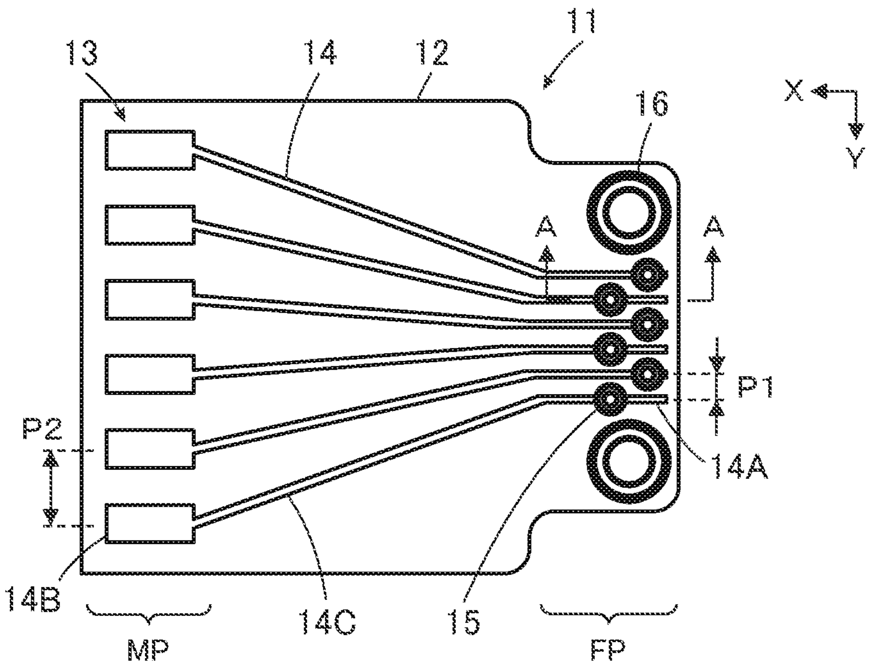
FIG. 2 is a plan view showing a connector used in Embodiment 1.

As shown in FIG. 2, the connector 11 includes a substantially rectangular sheet member 12. The sheet member 12 includes a fitting portion FP that is arranged at the −X-direction-side portion and is fitted to the counter connector 21, and a mounting portion MP that is arranged at the +X-direction-side portion and is mounted on the garment G, and the fitting portion FP is formed to have a narrower width in the Y direction than that of the mounting portion MP.

The sheet member 12 is a flexible member made of insulating cloth or knitted fabric, for example, and is provided with an embroidery pattern 13 embroidered with embroidery threads.

By using a conductive thread as the embroidery thread to form the embroidery pattern 13, a plurality of flexible conductors 14 having conductivity are formed on at least the top surface of the sheet member 12. For example, of the embroidery threads, a conductive thread is used only for a part exposed on the top surface on the +Z direction side of the sheet member 12, while an insulating thread is used for a part exposed on the bottom surface on the −Z directional side of the sheet member 12, whereby the flexible conductors 14 can be formed to be disposed at least on the top surface of the sheet member 12.

Each flexible conductor 14 includes a linear first connection portion 14A disposed in the fitting portion FP of the sheet member 12 and extending in the X direction, a rectangular second connection portion 14B disposed in the mounting portion MP of the sheet member 12, and a joint portion 14C joining the first connection portion 14A and the second connection portion 14B to each other.

The first connection portions 14A of the plurality of flexible conductors 14 are linearly aligned along the Y direction at a predetermined alignment pitch P1, and the second connection portions 14B of the flexible conductors 14 are linearly aligned along the Y direction at an alignment pitch P2 that is larger than the alignment pitch P1 of the first connection portions 14A.

The second connection portion 14B of each flexible conductor 14 has a wider width in the Y direction than that of the first connection portion 14A.

The connector 11 includes a plurality of contact members 15 attached to the fitting portion FP of the sheet member 12 and electrically connected to the first connection portions 14A of the flexible conductors 14.

Each contact member 15 is a ring-shaped conductive member made of, for example, metal and attached to the sheet member 12 so as to be superposed on the first connection portion 14A of the corresponding flexible conductor 14. The contact members 15 are arranged in a so-called staggered manner so as not to be short-circuited to one another.

The connector 11 further includes a pair of positioning members 16 disposed on the +Y direction side and the −Y direction side of the contact members 15 in the fitting portion FP of the sheet member 12. The positioning members 16 are used to position the sheet member 12 with respect to the counter connector 21.

As shown in FIGS. 3 and 4, each ring-shaped contact member 15 is attached to a peripheral portion of a contact through-hole 12A formed in the sheet member 12 where the first connection portion 14A of the corresponding flexible conductor 14 is disposed. As the contact member 15, for example, a ring-shaped metal part so-called "grommet" can be used.

As shown in FIG. 3, each positioning member 16 is a ring-shaped member attached to the periphery of a positioning through-hole 12B formed in the fitting portion FP of the sheet member 12 and is more rigid than the flexible sheet member 12. Accordingly, the positioning member 16 also works to reinforce the vicinity of the positioning through-hole 12B. As the positioning member 16, for example, a ring-shaped metal part so-called "grommet" that is larger than the contact member 15 can be used.

As shown in FIG. 5, the counter connector 21 includes a connector body 22, and a lid body 23 that is attached to the connector body 22 to be openable and closable.

The connector body 22 is made of an insulating material, includes a base portion 22A extending in the Y direction at the −X directional end of the connector body 22, and a flat plate portion 22B extending from the base portion 22B toward the +X direction. The flat plate portion 22B is provided in its +Z directional surface with a recess portion 22C opening toward the +X direction.

In the recess portion 22C of the flat plate portion 22B, a plurality of counter contacts 24 are disposed. The counter contacts 24 correspond to the contact members 15 of the connector 11 and are arranged in a so-called staggered manner as with the contact members 15.

In addition, in the recess portion 22C of the flat plate portion 22B, a pair of positioning pins 22D disposed on the +Y direction side and the −Y direction side of the counter contacts 24 are formed to protrude toward the +Z direction.

The lid body 23 is attached to the base portion 22A, and is rotated about a rotation axis extending in the Y direction, whereby the +Z directional surface of the flat plate portion 22B can be opened or closed.

Figure 6:
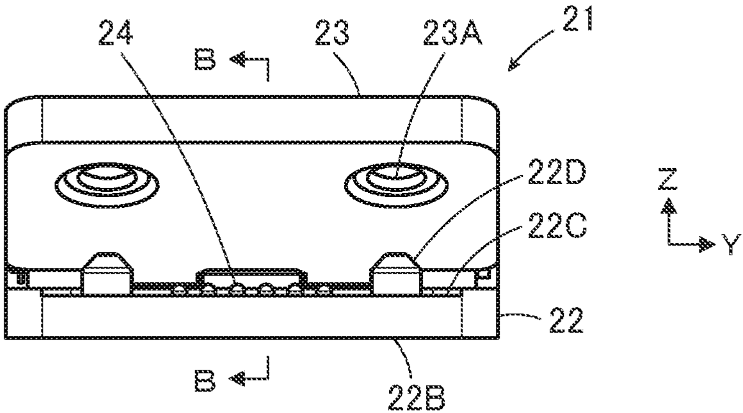
FIG. 6 is a front view showing the counter connector used in Embodiment 1.

As shown in FIG. 6, the counter contacts 24 each protrude in the +Z direction from the recess portion 22C of the flat plate portion 22B.

The lid body 23 is provided with a pair of pin accommodation holes 23A in which the pair of positioning pins 22D of the flat plate portion 22B are accommodated when the +Z directional surface of the flat plate portion 22B is closed.

Figure 7:
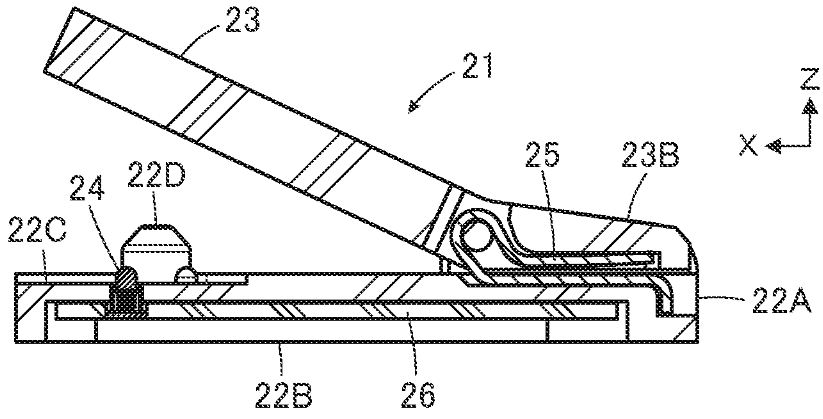
FIG. 7 is a cross-sectional view taken along line B-B in FIG. 6.

As shown in FIG. 7, in the base portion 22A, disposed is a lid body spring member 25 for pressing the lid body 23 toward the +Z directional surface of the flat plate portion 22B. When a pressing portion 23B formed at the −X directional end of the lid body 23 is pressed down in the −Z direction toward the base portion 22A of the connector body 22 against the elastic force of the lid body spring member 25, the +X directional portion of the lid body 23 is lifted in the +Z direction, and the +Z directional surface of the flat plate portion 22B is thus opened, whereas, when the pressing force acting on the pressing portion 23B is removed, the elastic force of the lid body spring member 25 causes the +X directional portion of the lid body 23 to fall in the −Z direction, and the +Z directional surface of the flat plate portion 22B is thus closed.

As also shown in FIG. 7, in the connector body 22, a module substrate 26 is disposed inside the flat plate portion 22B, and the counter contacts 24 are attached to the module substrate 26.

Figure 8:
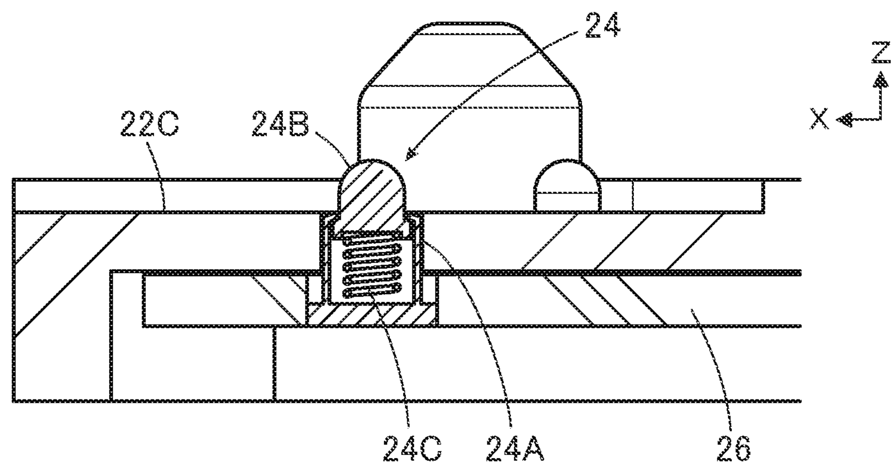
FIG. 8 is an enlarged view of a main part of FIG. 7.

As shown in FIG. 8, each counter contact 24 includes a barrel 24A extending in the Z direction, a plunger 24B disposed to be movable forward and backward in the Z direction in the barrel 24A, and a contact spring member 24C applying the elastic force in the +Z direction to the plunger 24B. The plunger 24B is configured such that, with the +Z directional end thereof protruding in the +Z direction from the surface of the recess portion 22C of the flat plate portion 22B, the plunger 24B elastically moves forward and backward in the Z direction due to the action of the contact spring member 24C.

When the connector 11 is fitted to the counter connector 21, as shown in FIG. 7, the pressing portion 23B of the lid body 23 of the counter connector 21 is pressed down in the −Z direction, whereby the +X directional portion of the lid body 23 is lifted in the +Z direction, the +Z directional surface of the flat plate portion 22B is opened, and in this state, the fitting portion FP of the sheet member 12 of the connector 11 is inserted between the flat plate portion 22B and the lid body 23 from the +X direction.

By fitting the pair of positioning members 16 formed in the fitting portion FP of the sheet member 12 of the connector 11 with the pair of positioning pins 22D formed in the recess portion 22C of the flat plate portion 22B of the counter connector 21, the contact members 15 of the connector 11 are positioned at the counter contacts 24 of the counter connector 21 to be situated on the plungers 24B of the counter contacts 24.

Since the positioning members 16 are more rigid than the sheet member 12, by fitting the positioning members 16 with the positioning pins 22D of the counter connector 21, the fitting portion FP of the sheet member 12 can be assured to be positioned with respect to the counter contacts 24 even when the sheet member 12 is formed of flexible cloth or knitted fabric.

In this state, when the pressing force acting on the pressing portion 23B of the lid body 23 of the counter connector 21 is removed, the elastic force of the lid body spring member 25 causes the +X directional portion of the lid body 23 to fall in the −Z direction, and as shown in FIG. 9, the fitting portion FP of the sheet member 12 of the connector 11 is pressed toward the flat plate portion 22B of the counter connector 21.

Hence, as shown in FIG. 10, the contact member 15 of the connector 11 elastically presses the plunger 24B down in the −Z direction against the elastic force of the contact spring member 24C of the corresponding counter contact 24 of the counter connector 21 and makes contact with the plunger 24B with a predetermined contact pressure. As a result, the contact member 15 of the connector 11 is electrically connected to the corresponding counter contact 24 of the counter connector 21.

As shown in FIG. 1, the bottom surface of the garment G, i.e., a mounting object, is provided with a plurality of conductive wiring portions G1 corresponding to the plurality of flexible conductors 14 of the connector 11, and when the second connection portions 14B disposed in the mounting portion MP of the sheet member 12 of the connector 11 are each sewn to an end of the corresponding wiring portion G1 of the garment G using, for example, a conductive sewing thread, the flexible conductors 14 are separately and electrically connected to the wiring portions G1 of the garment G.

As a result, the counter contacts 24 of the counter connector 21 can be separately and electrically connected to the wiring portions G1 of the garment G via the contact members 15 and the flexible conductors 14 of the connector 11.

The other ends of the wiring portions G1 each extend along the bottom surface of the garment G up to an electrode (not shown) attached to the garment G.

Hence, when a predetermined electronic circuit is mounted on the module substrate 26 included in the counter connector 21, biological data acquired through the electrode can be measured by the electronic circuit or transmitted to a remote measurement device from the electronic circuit.

In the connector 11 in Embodiment 1, since the flexible sheet member 12 formed of insulating cloth or knitted fabric has a sheet shape in which the flexible conductors 14, the ring-shaped contact members 15, and the pair of ring-shaped positioning members 16 are disposed, when the connector 11 is mounted on the garment G, a user does not feel unconformable, and it is possible to suppress deterioration in comfortableness in wearing the garment G.

In addition, by mounting the connector 11 to an outside of the garment G, it is possible to suppress deterioration in comfortableness in wearing the garment G when the connector 11 is fitted to the counter connector 21.

Embodiment 2

In Embodiment 1 described above, the contact members 15 attached to the sheet member 12 of the connector 11 are each composed of a ring-shaped conductive member, but the invention is not limited thereto.

FIG. 11 shows a connector 31 used in Embodiment 2. The connector 31 is configured such that in the connector 11 in Embodiment 1, in place of the contact members 15, a plurality of contact members 35 are attached to the fitting portion FP of the sheet member 12; the connector 31 is otherwise configured similarly to the connector 11. That is, the flexible conductors 14 are formed on the sheet member 12, and the contact members 35 and the pair of positioning members 16 are disposed in the fitting portion FP of the sheet member 12.

Figure 12:
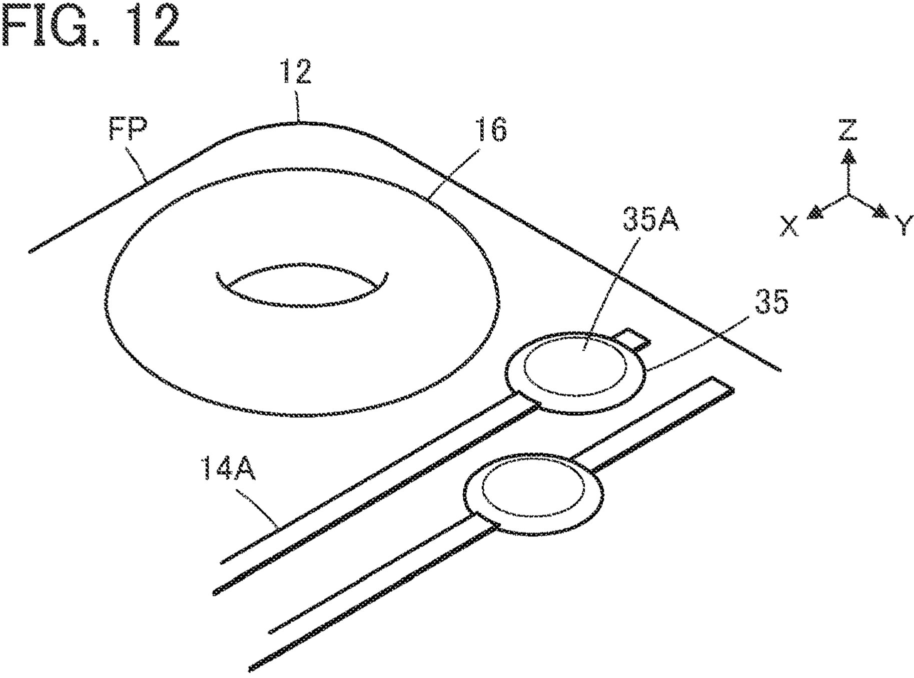
FIG. 12 is a partial perspective view showing the connector used in Embodiment 2.
Figure 13:
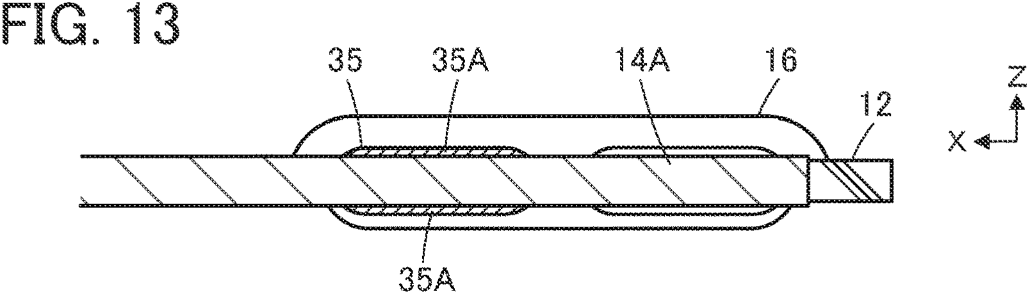
FIG. 13 is a cross-sectional view taken along line C-C in FIG. 11.

As shown in FIGS. 12 and 13, each contact member 35 includes a pair of flat plate-shaped conductive portions 35A separately exposed on the top surface on the +Z direction side and the bottom surface on the −Z direction side of the sheet member 12, and does not have a center hole that the ring-shaped contact member 15 in Embodiment 1 has.

When the connector 31 is fitted to the counter connector 21 used in Embodiment 1, the conductor portion 35A of the contact member 35 exposed on the bottom surface of the sheet member 12 of the connector 31 is pressed against the plunger 24B of the corresponding counter contact 24 of the counter connector 21, and the contact member 35 of the connector 31 is electrically connected to the corresponding counter contact 24 of the counter connector 21.

With the connector 31 being mounted on the garment G, the counter contacts 24 of the counter connector 21 thus can be separately and electrically connected to the wiring portions G1 of the garment G while suppressing deterioration in comfortableness in wearing the garment G as with Embodiment 1.

Embodiment 3

Figure 14:
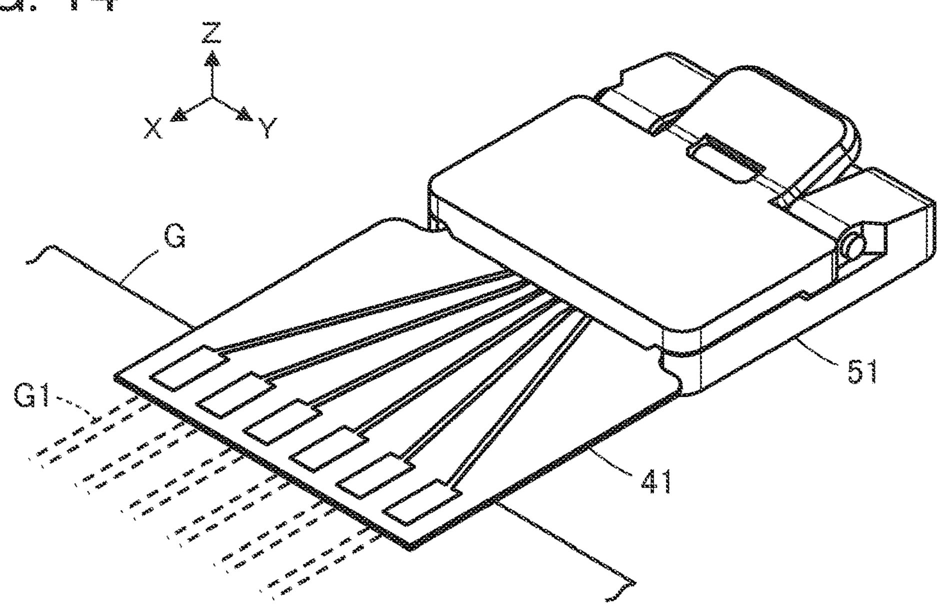
FIG. 14 is a perspective view showing a connector assembly according to Embodiment 3.

FIG. 14 shows a connector assembly according to Embodiment 3. The connector assembly includes a connector 41 and a counter connector 51 to which the connector 41 is fitted.

Figure 15:
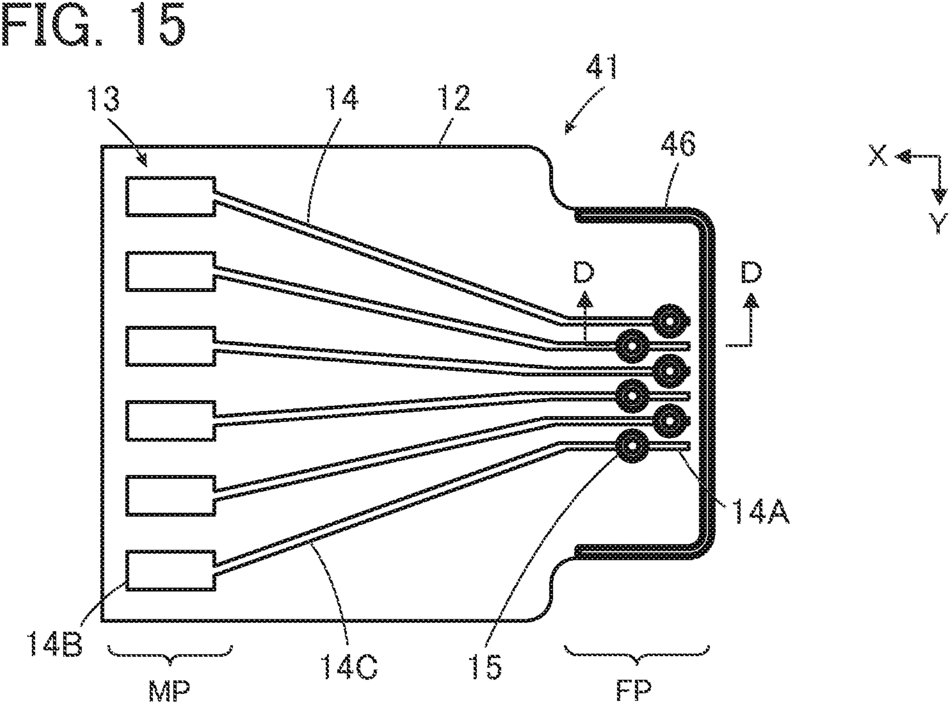
FIG. 15 is a plan view showing a connector used in Embodiment 3.

As shown in FIG. 15, the connector 41 is configured such that in the connector 11 in Embodiment 1, in place of the pair of positioning members 16, a positioning member 46 is attached to the periphery of the fitting portion FP of the sheet member 12; the connector 41 is otherwise configured similarly to the connector 11. That is, the flexible conductors 14 are formed on the sheet member 12, and the contact members 15 and the positioning member 46 are disposed in the fitting portion FP of the sheet member 12.

Figure 16:
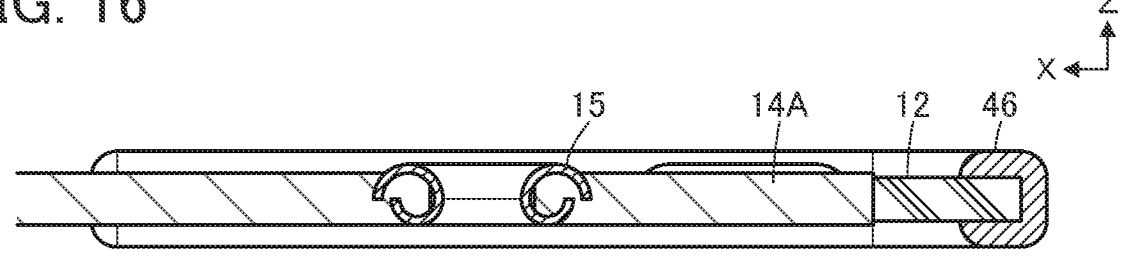
FIG. 16 is a cross-sectional view taken along line D-D in FIG. 15.

The positioning member 46 is composed of a frame-shaped member disposed at the periphery of the fitting portion FP of the sheet member 12, specifically, disposed continuously along the −Y directional edge, the −X directional edge, and the +Y directional edge of the fitting portion FP. As shown in FIG. 16, the positioning member 46 surrounds the edge of the sheet member 12 from the top surface on the +Z direction side of the sheet member 12 to the bottom surface on the −Z direction side of the sheet member 12 through the lateral surface of the sheet member 12 in the cross section perpendicular to the direction in which the positioning member 46 extends.

As the positioning member 46, a frame-shaped metal part formed of a bent metal sheet can be used. The positioning member 46 as above is attached to the fitting portion FP of the sheet member 12, whereby the rigidity of the fitting portion FP can be improved to reinforce the fitting portion FP.

Figure 17:
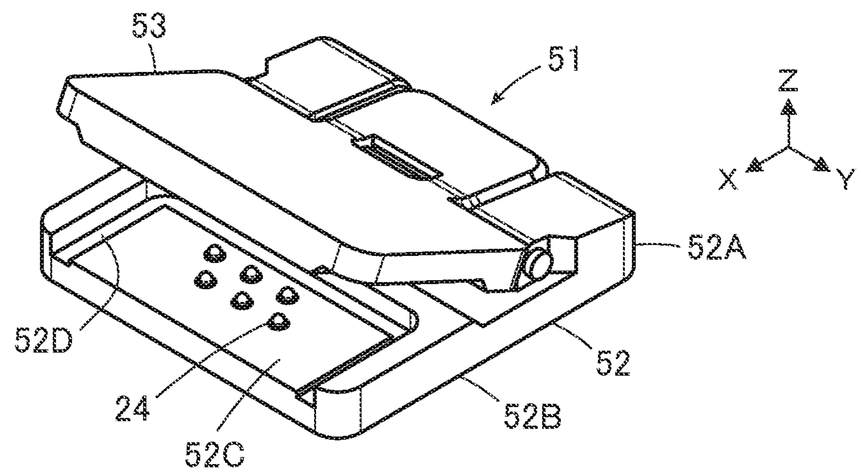
FIG. 17 is a perspective view showing a counter connector used in Embodiment 3.

As shown in FIG. 17, as with the counter connector 21 used in Embodiment 1, the counter connector 51 includes a connector body 52, and a lid body 53 that is attached to the connector body 52 to be openable and closable. The connector body 52 includes a base portion 52A and a flat plate portion 52B. The flat plate portion 52B is provided in its +Z directional surface with a recess portion 52C opening toward the +X direction, and in the recess portion 52C, the counter contacts 24 are disposed.

In addition, in the counter connector 51, a positioning groove portion 52D is formed around the recess portion 52C of the flat plate portion 52B.

Figure 18:
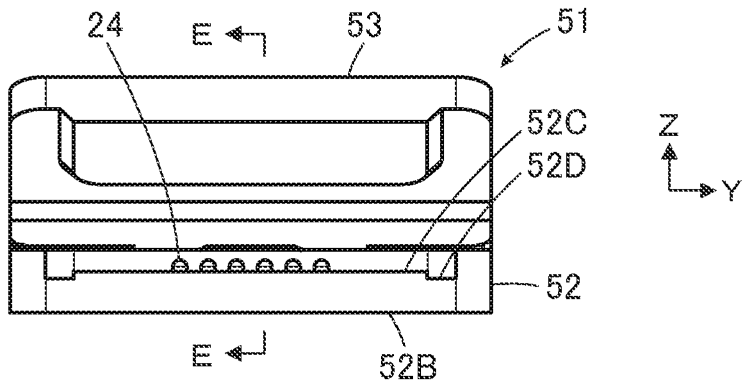
FIG. 18 is a front view showing the counter connector used in Embodiment 3.

As shown in FIG. 18, the counter contacts 24 each protrude in the +Z direction from the recess portion 52C of the flat plate portion 52B.

Figure 19:
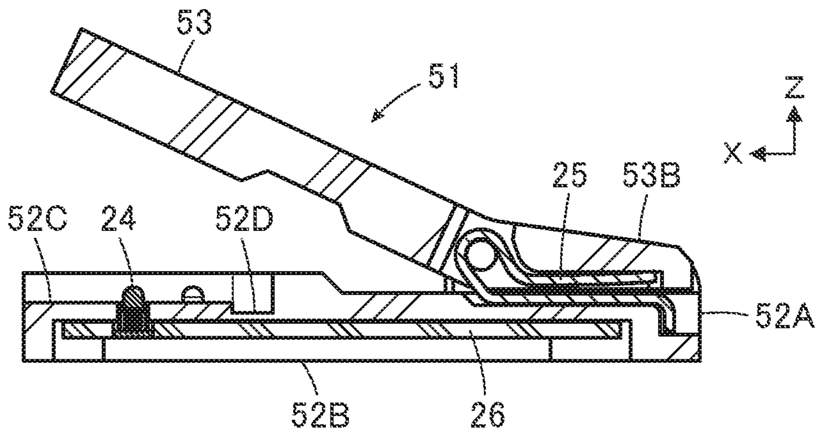
FIG. 19 is a cross-sectional view taken along line E-E in FIG. 18.

Moreover, the lid body spring member 25 is disposed in the base portion 52A as shown in FIG. 19, and as with the counter connector 21 used in Embodiment 1, when a pressing portion 53B formed at the −X directional end of the lid body 53 is pressed down in the −Z direction toward the base portion 52A of the connector body 52 against the elastic force of the lid body spring member 25, the +X directional portion of the lid body 53 is lifted in the +Z direction, and the +Z directional surface of the flat plate portion 52B is thus opened, whereas, when the pressing force acting on the pressing portion 53B is removed, the elastic force of the lid body spring member 25 causes the +X directional portion of the lid body 53 to fall in the −Z direction, and the +Z directional surface of the flat plate portion 52B is thus closed.

When the connector 41 is fitted to the counter connector 51, as shown in FIG. 19, the +X directional portion of the lid body 53 of the counter connector 51 is lifted in the +Z direction, the +Z directional surface of the flat plate portion 52B is opened, and in this state, the fitting portion FP of the sheet member 12 of the connector 41 is inserted between the flat plate portion 52B and the lid body 53 from the +X direction.

By fitting the positioning member 46 attached to the fitting portion FP of the sheet member 12 of the connector 41 into the positioning groove portion 52D formed around the recess portion 52C of the flat plate portion 52B of the counter connector 51, the contact members 15 of the connector 41 are positioned at the counter contacts 24 of the counter connector 51 to be situated on the plungers 24B of the counter contacts 24.

Since the positioning member 46 is composed of, for example, a frame-shaped metal part and is more rigid than the sheet member 12, by fitting the positioning member 46 into the positioning groove portion 52D of the counter connector 51, the fitting portion FP of the sheet member 12 can be assured to be positioned with respect to the counter contacts 24 even when the sheet member 12 is formed of flexible cloth or knitted fabric.

Figure 20:
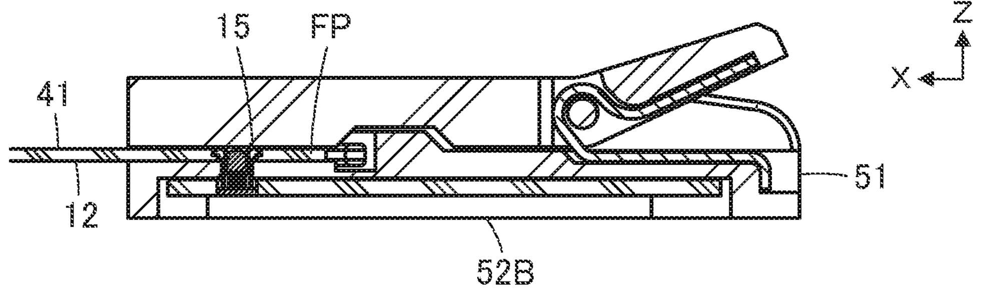
FIG. 20 is a partial cross-sectional view showing the connector assembly according to Embodiment 3.

In this state, when the pressing force acting on the pressing portion 53B of the lid body 53 of the counter connector 51 is removed, the elastic force of the lid body spring member 25 causes the +X directional portion of the lid body 53 to fall in the −Z direction, and as shown in FIG. 20, the fitting portion FP of the sheet member 12 of the connector 41 is pressed toward the flat plate portion 52B of the counter connector 51.

Figure 21:
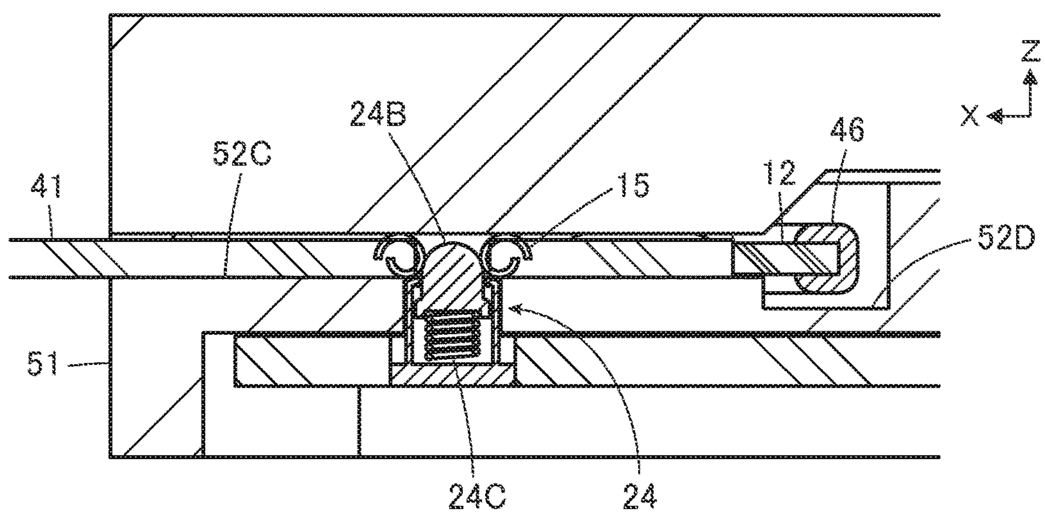
FIG. 21 is an enlarged view of a main part of FIG. 20.

Hence, as shown in FIG. 21, the contact member 15 of the connector 41 elastically presses the plunger 24B down in the −Z direction against the elastic force of the contact spring member 24C of the corresponding counter contact 24 of the counter connector 51 and makes contact with the plunger 24B with a predetermined contact pressure. As a result, the contact member 15 of the connector 41 is electrically connected to the corresponding counter contact 24 of the counter connector 51.

Even in Embodiment 3, the connector 41 is mounted on the garment G, whereby the counter contacts 24 of the counter connector 51 can be separately and electrically connected to the wiring portions G1 of the garment G while suppressing deterioration in comfortableness in wearing the garment G as with Embodiment 1.

Embodiment 4

Figure 22:
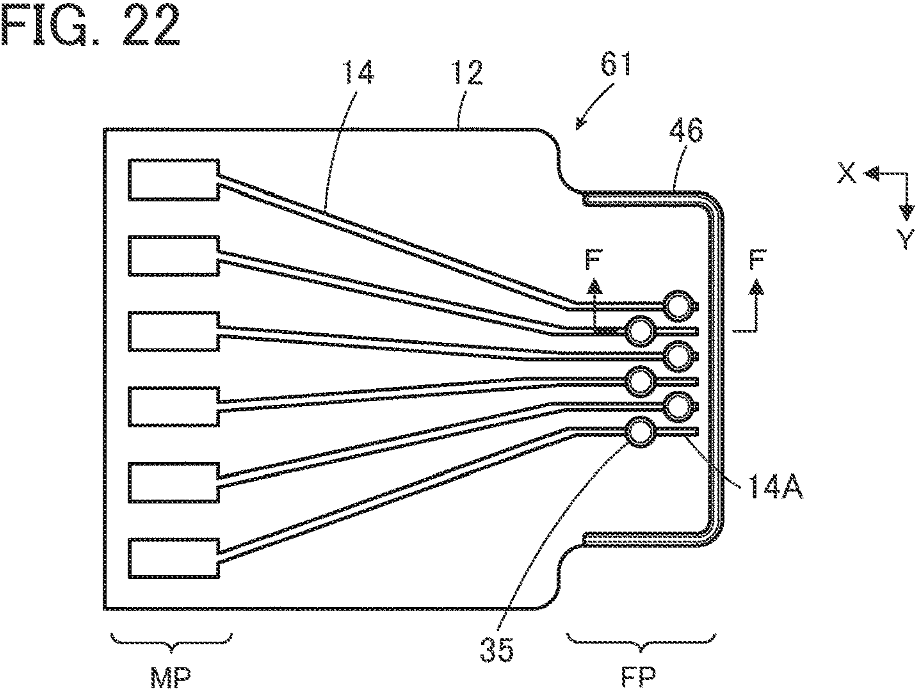
FIG. 22 is a plan view showing a connector used in Embodiment 4.

FIG. 22 shows a connector 61 used in Embodiment 4. The connector 61 is configured such that in the connector 41 in Embodiment 3, in place of the contact members 15, the contact members 35 are attached to the fitting portion FP of the sheet member 12; the connector 61 is otherwise configured similarly to the connector 41. That is, the flexible conductors 14 are formed on the sheet member 12, and the contact members 35 and the frame-shaped positioning member 46 are disposed in the fitting portion FP of the sheet member 12.

Figure 23:
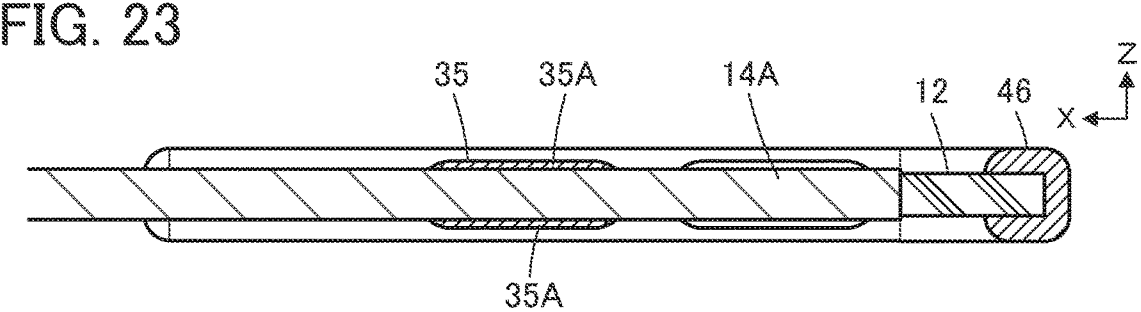
FIG. 23 is a cross-sectional view taken along line F-F in FIG. 22.

The contact members 35 are identical to the contact members 35 used in Embodiment 2 and each include, as shown in FIG. 23, a pair of flat plate-shaped conductive portions 35A separately exposed on the top surface on the +Z direction side and the bottom surface on the −Z direction side of the sheet member 12.

When the connector 61 is fitted to the counter connector 51 used in Embodiment 3, the conductor portion 35A of the contact member 35 exposed on the bottom surface of the sheet member 12 of the connector 61 is pressed against the plunger 24B of the corresponding counter contact 24 of the counter connector 51, and the contact member 35 of the connector 61 is electrically connected to the corresponding counter contact 24 of the counter connector 51.

With the connector 61 being mounted on the garment G, the counter contacts 24 of the counter connector 51 thus can be separately and electrically connected to the wiring portions G1 of the garment G while suppressing deterioration in comfortableness in wearing the garment G as with Embodiment 3.

Embodiment 5

Figure 24:
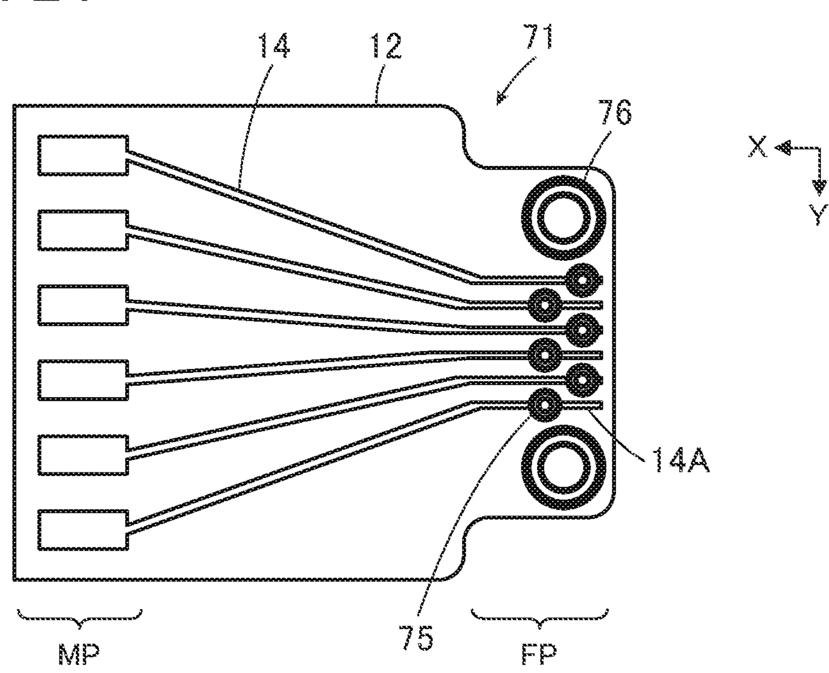
FIG. 24 is a plan view showing a connector used in Embodiment 5.

FIG. 24 shows a connector 71 used in Embodiment 5. The connector 71 is configured such that in the connector 11 in Embodiment 1, in place of the contact members 15 and the pair of positioning members 16, a plurality of contact members 75 and a pair of positioning members 76 are attached to the fitting portion FP of the sheet member 12; the connector 71 is otherwise configured similarly to the connector 11. That is, the flexible conductors 14 are formed on the sheet member 12, and the contact members 75 and the pair of positioning members 76 are disposed in the fitting portion FP of the sheet member 12.

The contact members 75 and the pair of positioning members 76 are each formed of a conductive thread embroidered on or woven into the sheet member 12. While the flexible conductors 14 are also formed of embroidery using a conductive thread, the contact members 75 and the positioning members 76 are formed by embroidering or weaving multiple layers of conductive threads to the sheet member 12, thereby being thicker and more rigid than the flexible conductors 14.

In addition, as with the contact members 15 and the positioning members 16 in Embodiment 1, the contact members 75 and the positioning members 76 each have a ring shape, and each contact member 75 and each positioning member 76 are respectively attached to the peripheral portion of the contact through-hole 12A and the peripheral portion of the positioning through-hole 12B formed in the sheet member 12 as shown in FIG. 3.

Hence, when the connector 71 is fitted to the counter connector 21 used in Embodiment 1, as with Embodiment 1, by fitting the pair of positioning members 76 formed in the fitting portion FP of the sheet member 12 of the connector 71 with the pair of positioning pins 22D of the counter connector 21, the contact members 75 of the connector 71 can be positioned at the counter contacts 24 of the counter connector 21.

In addition, the plunger 24B of each counter contact 24 of the counter connector 21 is elastically pressed against and makes contact with the corresponding contact member 75 of the connector 71 with a predetermined contact pressure. As a result, the contact members 75 of the connector 71 are electrically connected to the counter contacts 24 of the counter connector 21.

With the connector 71 being mounted on the garment G, the counter contacts 24 of the counter connector 21 thus can be separately and electrically connected to the wiring portions G1 of the garment G while suppressing degrading of comfortableness in wearing the garment G as with Embodiment 1.

It should be noted that even when a flat plate-shaped contact member having a different shape from a ring shape and having no center hole such as the contact member 35 in Embodiment 2 is formed of a conductive thread embroidered on or woven into the sheet member 12, the counter contacts 24 of the counter connector 21 can be also separately and electrically connected to the wiring portions G1 of the garment G while suppressing deterioration in comfortableness in wearing the garment G.

In addition, even when a positioning member disposed at the periphery of the fitting portion FP of the sheet member 12 such as the positioning member 46 in Embodiment 3 is formed of a conductive thread embroidered on or woven into the sheet member 12, the connector can be positioned with respect to the counter connector 51, and a similar connector assembly to that in Embodiment 3 can be configured.

In Embodiment 5 described above, the contact members 75 and the positioning members 76 are both formed of a conductive thread embroidered on or woven into the sheet member 12; however, either the contact members 75 or the positioning members 76 may be formed of a conductive thread.

Embodiment 6

Figure 25:
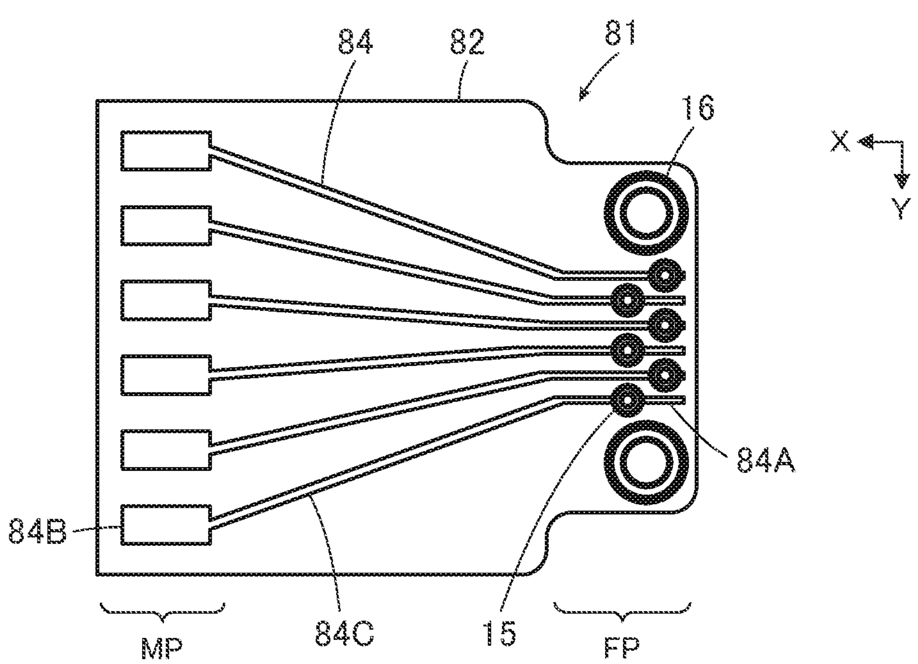
FIG. 25 is a plan view showing a connector used in Embodiment 6.
Figure 26:
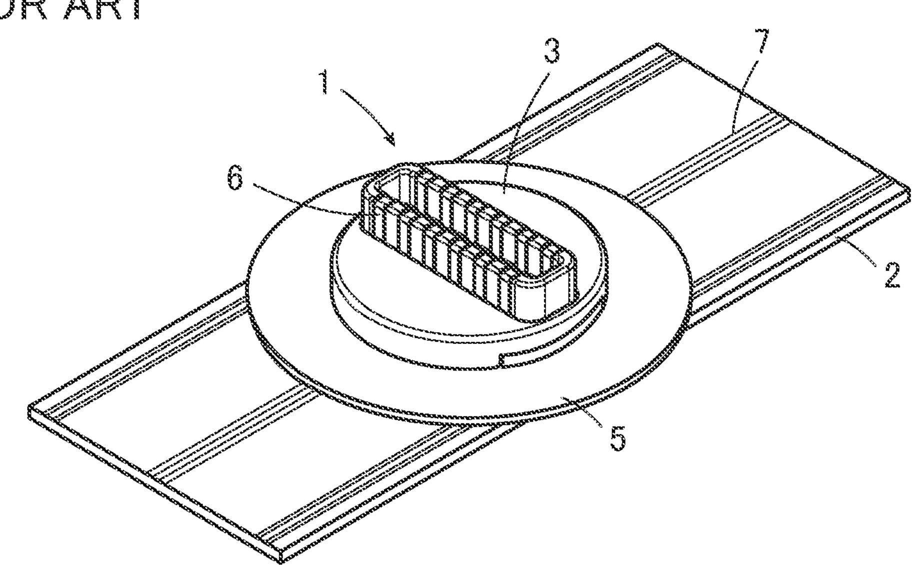
FIG. 26 is a perspective view of a conventional connector when viewed from an obliquely upper position.
Figure 27:
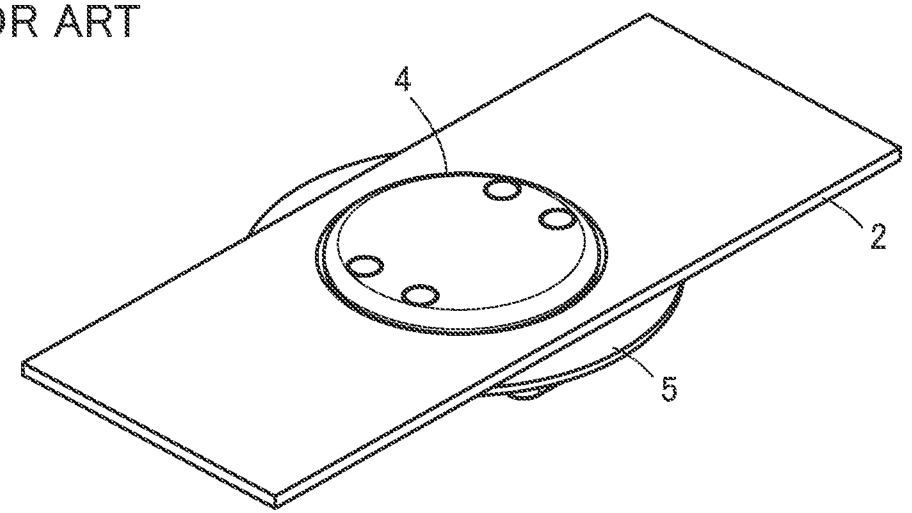
FIG. 27 is a perspective view of the conventional connector when viewed from an obliquely lower position.

FIG. 25 shows a connector 81 used in Embodiment 6. The connector 81 is configured such that in the connector 11 in Embodiment 1, used are a sheet member 82 formed of a flexible and insulating resin film and a plurality of flexible conductors 84 formed of a conductive layer disposed on the sheet member 82 in place of the sheet member 12 formed of insulating cloth or knitted fabric and the plurality of flexible conductors 14 formed of embroidery using a conductive thread, respectively; the connector 81 is otherwise configured similarly to the connector 11.

As with the sheet member 12 in Embodiment 1, the sheet member 82 includes the fitting portion FP arranged at the −X-direction-side portion, and the mounting portion MP arranged at the +X-direction-side portion.

Moreover, as with the flexible conductors 14 in Embodiment 1, the flexible conductors 84 each include a linear first connection portion 84A disposed in the fitting portion FP of the sheet member 82 and extending in the X direction, a rectangular second connection portion 84B disposed in the mounting portion MP of the sheet member 82, and a joint portion 84C joining the first connection portion 84A and the second connection portion 84B to each other.

The contact members 15 are separately and electrically connected to the first connection portions 84A of the flexible conductors 84.

Even when the connector 81 as described above is mounted on the garment G, the counter contacts 24 of the counter connector 21 can be separately and electrically connected to the wiring portions G1 of the garment G while suppressing deterioration in comfortableness in wearing the garment G as with Embodiment 1.

In the connector 81, a plurality of flat plate-shaped contact members 35 used in Embodiment 2 can be used in place of the ring-shaped contact members 15, and the frame-shaped positioning member 46 used in Embodiment 3 can be used in place of the pair of ring-shaped positioning members 16.

It should be noted that in each of Embodiments 1, 2, and 5, the contact members 15, 35, or 75 are arranged in a staggered manner, but the invention is not limited thereto, and the contact members may be arranged in one row. Moreover, this invention does not necessarily require the plurality of contacts members 15, 35, 75, and it suffices if at least one contact member is provided.

In addition, in Embodiments 1 to 6 described above, the connector 11, 31, 41, 61, 71, 81 is mounted on the garment G as the mounting object, whereby the counter contacts 24 of the counter connector 21, 51 can be separately and electrically connected to the wiring portions G1 of the garment G while suppressing deterioration in comfortableness in wearing the garment G, but the mounting object is not limited to the garment G. For instance, when the connector according to the invention is mounted on a bag or another item the user carries or wears, the counter connector 21, 51 can be fitted to the connector without generating uncomfortableness, and when the connector according to the invention is mounted on a sheet, a bed, or a bedding piece on or in which the user lies, the counter connector 21, 51 can be fitted to the connector without degrading comfortableness.

What is claimed is:

1. A connector configured to be mounted on a mounting object and fitted to a counter connector, the mounting object having a wiring portion disposed thereon, the connector comprising:

a sheet member having flexibility and insulating property;

a flexible conductor disposed at least on a top surface of the sheet member;

a contact member having conductivity that is attached to the sheet member and configured to be electrically connected to a counter contact of the counter connector; and a positioning member configured to position the sheet member with respect to the counter connector, wherein the sheet member includes a fitting portion to be fitted to the counter connector, and a mounting portion to be mounted on the mounting object, the contact member and the positioning member are disposed in the fitting portion of the sheet member, and the flexible conductor includes a first connection portion disposed in the fitting portion of the sheet member and electrically connected to the contact member, a second connection portion disposed in the mounting portion of the sheet member and to be electrically connected to the wiring portion of the mounting object, and a joint portion joining the first connection portion and the second connection portion to each other, wherein the positioning member is composed of a frame-shaped member attached to a periphery of the fitting portion of the sheet member so as to surround the fitting portion, and the positioning member is to be fitted in a positioning groove portion formed in the counter connector, whereby the sheet member is positioned with respect to the counter connector.

2. The connector according to claim 1, wherein the contact member is composed of a ring-shaped conductive member attached to a peripheral portion of a contact through-hole formed in the fitting portion of the sheet member.

3. The connector according to claim 1, wherein the contact member includes a conductive portion of flat plate shape attached to the fitting portion of the sheet member.

4. The connector according to claim 1, wherein the sheet member is formed of cloth or knitted fabric, and the flexible conductor is formed of a conductive thread embroidered on or woven into the sheet member.

5. The connector according to claim 4, wherein the contact member is formed of a conductive thread embroidered on or woven into the sheet member.

6. The connector according to claim 1, wherein the sheet member is formed of an insulating resin film, and the flexible conductor is formed of a conductive layer disposed on the sheet member.

7. The connector according to claim 1, wherein the positioning member is composed of a ring-shaped member attached to a periphery of a positioning through-hole formed in the fitting portion of the sheet member, and the positioning through-hole and the positioning member are to be fitted with a positioning pin formed in the counter connector, whereby the sheet member is positioned with respect to the counter connector.

8. The connector according to claim 1, wherein the connector is to be mounted on a garment as the mounting object.

9. A connector comprising:

the connector according to claim 1; and the counter connector to which the connector is fitted.

10. The connector according to claim 9, wherein the counter connector includes a connector body in which the counter contact is disposed, and a lid body that is attached to the connector body to be openable and closable, and the fitting portion of the sheet member of the connector disposed on the counter contact is pressed toward the connector body by the lid body, whereby the contact member of the connector is electrically connected to the counter contact of the counter connector.

11. The connector assembly according to claim 10, wherein the counter connector includes a lid body spring member that presses the lid body toward the connector body.

12. The connector according to claim 9, wherein the counter contact of the counter connector includes a plunger disposed to be movable forward and backward, and a contact spring member for elastically moving the plunger forward and backward.

* * * * *